United States Patent [19]

Straub et al.

[11] 4,350,791
[45] Sep. 21, 1982

[54] VINYLPYRROLIDONE POLYMERS, THEIR PREPARATION, THEIR USE IN THE PREPARATION OF PLASMA SUBSTITUTES, AND THE SUBSTITUTES THUS OBTAINED

[75] Inventors: Ferdinand Straub, Hockenheim; Siegfried Lang; Eckhard Roske, both of Ludwigshafen, all of Fed. Rep. of Germany

[73] Assignee: BASF Aktiengesellschaft, Fed. Rep. of Germany

[21] Appl. No.: 221,532

[22] Filed: Dec. 31, 1980

[30] Foreign Application Priority Data

Jan. 12, 1980 [DE] Fed. Rep. of Germany ....... 3001013

[51] Int. Cl.$^3$ .............................................. C08L 75/12
[52] U.S. Cl. ..................................... 525/123; 525/387
[58] Field of Search ......................................... 525/123

[56] References Cited

U.S. PATENT DOCUMENTS

| | | | |
|---|---|---|---|
| 3,931,111 | 1/1976 | Kopecek et al. | 260/67 R |
| 4,049,592 | 9/1977 | Marans et al. | 260/2.5 AD |
| 4,229,551 | 10/1980 | Straub | 525/337 |
| 4,254,239 | 3/1981 | Straub et al. | 525/123 |
| 4,277,576 | 7/1981 | Straub | 525/123 |

FOREIGN PATENT DOCUMENTS 2805525 8/1978 Fed. Rep. of Germany .
2831335 2/1980 Fed. Rep. of Germany .

OTHER PUBLICATIONS

S. J. Huang, et al., J. Appl. Polym. Sci. 23, (1979), Nr. 2, pp. 429–437.
S. J. Huang, et al., Polym. Prep. Amer. Chem. Soc. Div. Polym. Chem. 20, (1979), Nr. 2, pp. 552–554.

*Primary Examiner*—Paul Lieberman
*Attorney, Agent, or Firm*—Keil & Witherspoon

[57] ABSTRACT

Polymers which due to their physiological compatibility may be used in plasma substitutes and which essentially contain vinylpyrrolidone and $\alpha,\omega$-diisocyanatoalkanecarboxylic acid esters as structural units, their preparation, and plasma substitutes containing such polymers.

5 Claims, No Drawings

VINYLPYRROLIDONE POLYMERS, THEIR PREPARATION, THEIR USE IN THE PREPARATION OF PLASMA SUBSTITUTES, AND THE SUBSTITUTES THUS OBTAINED

First aid in cases of physiological shock frequently necessitates the use of plasma substitutes, since, in most cases, preserved blood is not immediately available. Furthermore, it is necessary to be able to replace the blood without any hazard arising from incompatibility in respect of blood group or rhesus factor. Pure salt solutions (such as physiological sodium chloride solution or Ringer solution) are unsuitable for the treatment of shock, because their residence time in the circulatory system is too low and because they lack the osmotic pressure associated with a colloid.

Polyvinylpyrrolidone solutions have been used extensively as a plasma substitute. Because of their similarity to peptides, polyvinylpyrrolidones are well tolerated in the body, and, given the appropriate mean molecular weight, their colloid-osmotic pressure resembles that of blood plasma. If the molecular weight of the polyvinylpyrrolidone is too high, the polymer is incompletely eliminated from the body and instead deposits in the reticulo-endothelium. If on the other hand a polymer consisting only of molecules of relatively low molecular weight is used as the plasma substitute, to ensure efficient elimination through the kidneys, the colloid-osmotic pressure, and hence the activity, are low. Polyvinylpyrrolidone is a very inert polymer, since it is polymerized by a free radical mechanism and accordingly the polymer chain consists of C—C bonds. These bonds are not attacked by the enzymes in the body (eg. in the blood or liver) and hence the polymers do not undergo degradation.

German Laid-Open Application DOS No. 2,759,150 and the corresponding U.S. patent application Ser. No. 973,798, filed Dec. 28, 1978, describe vinylpyrrolidone polymers and copolymers which are linked, by intermediate units containing ester, amide, urea or urethane groups, to give higher molecules, and which, because of their biological degradability, may be used to prepare plasma substitutes. U.S. Pat. No. 3,931,111 also describes high molecular weight products which are useful as degradable plasma substitutes, but these are not prepared from vinylpyrrolidone polymers. Since the enzymatic degradation of the known plasma substitutes may produce cleavage products whose physiological harmlessness has not hitherto been tested or proven, it is an object of the present invention to provide degradable polymers, suitable for use in plasma substitutes, whose cleavage products are physiologically acceptable.

We have found that this object is achieved by providing vinylpyrrolidone polymers of the general formula

[—A—B—]$_m$—A where

A is a chain of from 8 to about 1,000 vinylpyrrolidone molecules (i.e. structural units corresponding to the molecule), B is the radical of the $\alpha,\omega$-diisocyanate of an aliphatic alkane-1-carboxylic acid ester of 2 to 11 carbon atoms in the alkane moiety and of 2 to 10 carbon atoms in the ester moiety and m is from 1 to 50, the linkages between A and B being urethane groups formed from the hydroxyl groups on the vinylpyrrolidone chain and from the isocyanate groups.

These compounds are water-soluble block polymers which, surprisingly, on biological degradation give vinylpyrrolidone polymers and $\alpha,\omega$-diaminoalkanecarboxylic acids as cleavage products, though it was to be expected that either the esters would not be degraded or, if they were hydrolyzed, the acids formed would be further converted, to toxic amines, by the enzyme decarboxylase.

A vinylpyrrolidone polymer with hydroxyl end groups may be obtained by treating a polymer, obtained by free radical polymerization of N-vinylpyrrolid-2-one in the presence of hydrogen peroxide as a free radical initiator, with a complex hydride (German patent application P No. 28 31 335.1 of July 17, 1978). These vinylpyrrolidone polymers contain 2 hydroxyl end groups per macromolecule.

The starting compound is a polyvinylpyrrolidone which may be obtained in a conventional manner by polymerization of N-vinylpyrrolid-2-one in the presence of hydrogen peroxide, in aqueous solution; the procedures involved are known and reference may be made, for example, to the monograph by W. Reppe, "Polyvinylpyrrolidon", Verlag Chemie GmbH, Weinheim/Bergstrasse. The polymer is then treated with from 0.1 to 10%, preferably from 0.5 to 5%, based on weight of polymer, of a complex hydride. Preferably, a water-soluble hydride, eg. sodium boranate or lithium boranate, is used, but the reaction can also be carried out with others, eg. NaBH(OCH$_3$)$_3$, NaAlH$_4$, LiAlH$_4$, NaAlH$_2$(OCH$_2$OCH$_3$)$_2$ or LiAlH[OC(CH$_3$)$_3$]. The highly reactive complex hydride is only employed in such amount that the lactam group of the polyvinylpyrrolidone is not attacked. Preferably, the reaction with the complex hydride is carried out in water; this is feasible in the case of lithium boranate and sodium boranate. In the case of the other hydrides, it is advantageous to use a solvent, such as a lower alcohol, eg. methanol, ethanol, isopropanol, n-propanol, n-butanol or tert.-butanol, an ether, eg. dioxane or tetrahydrofuran, or an aromatic, eg. benzene, toluene or xylene. The reaction is carried out at from 1° to 150° C., preferably from 15° to 80° C., depending on the boiling point of the solvent. If the reaction is carried out in an aqueous or alcoholic solvent, the pH is in general brought to about 7 before the reaction. The reaction time varies from 0.5 to 24 hours, preferably from 2 to 8 hours.

The hydroxyl number of the vinylpyrrolidone polymer used to prepare the novel block polymer should conform to the equation $$\text{hydroxyl number found} = \frac{56,000}{M_n} \times 2$$

where $M_n$ = number-average molecular weight.

A vinylpyrrolidone polymer with hydroxyl groups may also be obtained by copolymerizing vinylpyrrolidone with such an amount of a hydroxyl-containing monomer that the polymer contains an average of 2 hydroxyl groups per macromolecule. Depending on the degree of polymerization of the vinylpyrrolidone polymer and the molecular weight of the hydroxyl-containing monomer, the proportion of the latter monomer is from about 0.1% by weight to about 12% by weight, based on vinylpyrrolidone. For example, in the case of allyl alcohol the figure is 5.4% by weight for a degree of polymerization of 9 and 0.5% by weight for a degree of polymerization of 90; for hydroxypropylmethacrylamide, the corresponding values are 12.5 and 1.4% by weight.

Examples of suitable hydroxyl-containing copolymerizable monomers are hydroxyethyl acrylate, 2-hydroxypropyl acrylate, allyl alcohol, N-2-hydroxyethyl-acrylamide, N-2-hydroxyethyl-methacrylamide, N-2-hydroxypropylacrylamide and N-2-hydroxypropylmethacrylamide. Accordingly, in the present context, the term vinylpyrrolidone polymer is to be understood to include copolymers of this type.

It is important that the vinylpyrrolidone polymer which is used to prepare the novel block polymers is substantially freed from impurities, such as water, pyrrolidone, amines and acids, which might, for their part, react with isocyanates. Suitable purification methods are cation exchange and anion exchange. Appropriate ion exchangers are marketed, for example, under the trademark Lewatit ®.

The number-average molecular weight of the purified vinylpyrrolidone polymer is determined by means of a vapor pressure osmometer. The average molecular weight of the vinylpyrrolidone polymer used to prepare the novel block polymers should be from about 888 to about 111,000, preferably from 1,000 to 10,000.

In determining the hydroxyl number using the equation given above, it is also important to use purified vinylpyrrolidone polymer.

$\alpha,\omega$-Diisocyanato-alkanecarboxylic acid esters of the indicated type may be obtained by the method of German Laid-Open Application DOS 1,418,995. Examples of such esters are ethyl 2,6-diisocyanatocaproate, propyl 2,6-diisocyanatocaproate, butyl 2,6-diisocyanatocaproate, octyl 2,6-diisocyanatocaproate, ethyl 2,5-diisocyanatovalerate and propyl 2,5-diisocyanatovalerate. Further examples are the corresponding propionic acid, butyric acid, caprylic acid and dodecanecarboxylic acid derivatives. The alcohol radicals in the ester may be selected from the aliphatic series ranging from ethanol to decanol, the alcohols from ethanol to hexanol being preferred. The caproic acid derivatives are preferred, since their degradation product is lysine.

The vinylpyrrolidone polymer and the diisocyanate should be used in about the stoichiometric amount, taking into account the desired value of m. If too little or too much diisocyanate is used, the desired molecular weight of the block polymer is not obtained. In general, 100 parts by weight of vinylpyrrolidone polymer require the use of $$\frac{M.W._{isocyanate} \times 100 \times \text{hydroxyl number}}{56,000 \times 2}$$

parts by weight of diisocyanate (M.W.=molecular weight); deviations of up to ±10% from this figure have very little or no effect on the end result.

The reaction of the vinylpyrrolidone polymer with the diisocyanate is advantageously carried out in an anhydrous reaction medium at from about 15° to 150° C., in the presence of a conventional catalyst for the formation of a urethane from an isocyanate. Examples of suitable solvents are aprotic solvents, eg. N-methylpyrrolidone, dimethylsulfoxide, dimethylformamide, toluene, dioxane, chlorohydrocarbons and mixtures of these. The preferred reaction temperatures are from about 25° to 100° C.

The value of m can be additionally regulated by varying the reaction time and temperature and the degree of purity of the vinylpyrrolidone polymer, in ways which are familiar to those skilled in the art. The value of m can be determined, during the reaction, by conventional methods of measurement.

Examples of suitable catalysts are tertiary amines and organic tin compounds, eg. triethylamine and dibutyltin laurate respectively.

The reaction of the vinylpyrrolidone polymer with the diisocyanate can also be carried out in the absence of a catalyst, but this involves longer reaction times, of up to several days at relatively low temperatures.

The block polymer obtained by reacting the vinylpyrrolidone polymer with the diisocyanate may be isolated by distilling off the solvent or by precipitation in a non-solvent, for example diethyl ether.

It is surprising that water-soluble block polymers are obtained by the method described, since it was to be expected that the carboxylic acid ester group in the diisocyanate would undergo trans-esterification reactions, thereby producing crosslinking, and that the hydrophobic ester group in the diisocyanate would produce an undesirable reduction in the solubility of the product in water.

The conventional methods for the preparation of pyrogen-free fluids may be used to prepare plasma substitutes from the novel block polymers. Mixtures with, for example, physiological sodium chloride solution or Ringer solution may also be prepared. The novel block polymers have the same effect as the polyvinylpyrrolidones conventionally used as plasma substitutes. In addition, however, they are biodegradable and give cleavage products which can be eliminated through the kidneys and are furthermore nontoxic. If, as described in the Example which follows, ethyl 2,6-diisocyanatocaproate is used, the cleavage product obtained is lysine, a compound which is essential to life.

EXAMPLE 1

(a) 50 parts (by weight, as are all the other parts referred to) of a polyvinylpyrrolidone prepared as described in 1(b), and having a K value of 17 and a hydroxyl number of 48, are dissolved in 300 parts of a 75:25 mixture of dioxane and toluene. 150 parts of solvent are distilled off and the residue is allowed to cool to 80° C. The pH of the solution (measured after dilution with water) is brought to 7.2 with triethylamine. 5 parts of ethyl 2,6-diisocyanatocaproate, dissolved in 20 parts of dioxane, are introduced in the course of 5 hours. The mixture is then stirred for 10 hours at 80° C., after which the polymer is precipitated by pouring the reaction solution into 1,000 parts of diethyl ether. The block polymer has a K value of 35.6 (measured on a 5% strength solution in water), corresponding to a calculated molecular weight of 85,700.

(b) 750 parts of vinylpyrrolidone are dissolved in 250 parts of water, 0.5 part of an 0.01% strength copper-II chloride solution and 30 parts of 30% strength hydrogen peroxide are added and the polymerization is carried out for 6 hours at 70° C. and a pH of 7.6. The polymer solution is then freeze-dried. The polymer obtained has a K value of 17, a hydroxyl number of 38, and a pyrrolidone content of 5.9%.

100 parts of this polymer are dissolved in 160 parts of water, the solution is brought to pH 7.5 with 10 parts by volume of ammonia, and 2 parts of sodium boranate are added, a little at a time. Whilst frothing continues (about 1 hour), the mixture is stirred at room temperature. It is then left to stand overnight and is purified over 2,000 parts of Lewatit S 100 and 2,000 parts of Lewatit M 500. Thereafter, it is freeze-dried. The polymer obtained has a hydroxyl number of 48 and contains 1.3% of pyrrolidone.

EXAMPLE 2

(a) The block polymer from 1(a), in the form of a 1.5% strength solution, is stirred for three days in a 1:1 mixture of blood plasma and water at pH 7.2 and 37° C. and the mixture is then freeze-dried. The product is suspended in a 1:3 mixture of methanol and methylene chloride and the suspension is left to stand for 20 minutes and then filtered. The filtrate is concentrated and the solid product obtained is taken up in $CH_2Cl_2$, precipitated with diethyl ether, filtered off and dried. This product has a K value of 27.4 (measured on a 5% strength solution in water), corresponding to a calculated molecular weight of 39,000.

(b) If the block polymer from 1(a) is heated for 3 days in a 5% strength aqueous NaOH solution at 100° C. and the hydrolysis products are determined by thin layer chromatography, lysine is detected as a degradation product.

Thin layer chromatography of the degradation products from 2(a) does not give meaningful information, since blood plasma itself contains lysine.

(c) If a 1.5% strength aqueous solution of the polymer is stirred for 3 days at pH 7.2 and 37° C. and is then freeze-dried, the product has a K value of 35.2 (measured on a 5% strength solution in water). This shows by comparison with the K value of Example 1(a) that treatment with water does not cause degradation of the block polymer.

We claim:
1. A vinylpyrrolidone polymer of the general formula
$$[-A-B-]_m-A$$
where
  A is a chain of from 8 to about 1,000 vinylpyrrolidone molecules,
  B is ethyl 2,6-diisocyanatocaproate and
  m is from 1 to 50,
the linkages between A and B being urethane groups formed from the hydroxyl groups on the vinylpyrrolidone chain and from the isocyanate groups.

2. A vinylpyrrolidone polymer as set forth in claim 1, wherein the vinylpyrrolidone component has been produced by treating a polymer, obtained by free radical polymerization of N-vinylpyrrolid-2-one in the presence of hydrogen peroxide as a free radical initiator, with a complex hydride.

3. A vinylpyrrolidone polymer as set forth in claim 1, wherein the vinylpyrrolidone component A has been obtained by copolymerizing the vinylpyrrolidone with an amount of a hydroxyl-containing monomer which is such that the polymer contains an average of 2 hydroxyl groups per macromolecule.

4. A process for the preparation of a vinylpyrrolidone polymer as set forth in claim 1, wherein a vinylpyrrolidone polymer containing from 8 to about 1,000 vinylpyrrolidone molecules and an average of 2 hydroxyl groups per macromolecule is reacted with ethyl 2,6-diisocyanatocaproate, in an amount which gives the required value m.

5. A plasma substitute which contains a vinylpyrrolidone polymer as described in claim 1.

* * * * *